United States Patent
Bonnet et al.

(10) Patent No.: US 11,045,657 B2
(45) Date of Patent: *Jun. 29, 2021

(54) LEADLESS-CAPSULE AUTONOMOUS CARDIAC IMPLANT COMPRISING AN ENERGY HARVESTER PROVIDING PHYSIOLOGICAL OR ACTIVITY INFORMATION ABOUT THE PATIENT

(71) Applicant: CAIRDAC, Antony (FR)

(72) Inventors: Jean-Luc Bonnet, Massy (FR);
Guillaume Ferin, Tours (FR)

(73) Assignee: CAIRDAC, Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/344,973

(22) PCT Filed: May 15, 2018

(86) PCT No.: PCT/EP2018/062485
§ 371 (c)(1),
(2) Date: Apr. 25, 2019

(87) PCT Pub. No.: WO2019/001829
PCT Pub. Date: Jan. 3, 2019

(65) Prior Publication Data
US 2020/0391038 A1 Dec. 17, 2020

(30) Foreign Application Priority Data
Jun. 28, 2017 (FR) .................................. 1755938

(51) Int. Cl.
*A61N 1/378* (2006.01)
*A61N 1/375* (2006.01)
*A61N 1/37* (2006.01)

(52) U.S. Cl.
CPC ......... *A61N 1/3785* (2013.01); *A61N 1/3704* (2013.01); *A61N 1/3756* (2013.01); *A61N 1/37512* (2017.08)

(58) Field of Classification Search
CPC .............. A61N 1/3785; A61N 1/37512; A61N 1/3704; A61N 1/3756
See application file for complete search history.

(56) References Cited

U.S. PATENT DOCUMENTS

2007/0293904 A1* 12/2007 Gelbart ................ A61N 1/3785
607/35
2009/0171408 A1 7/2009 Solem
(Continued)

*Primary Examiner* — Lindsey G Wehrheim
(74) *Attorney, Agent, or Firm* — Steven M. Greenberg, Esq.; Shutts & Bowen LLP

(57) ABSTRACT

An energy harvester converts into electrical energy the external stresses applied to the implant at the rhythm of the heartbeats. This harvester comprises an inertial unit. A transducer provides an oscillating electrical signal that is rectified and regulated, for powering the implant and/or charging a battery. The instantaneous variations of this electrical signal between two heartbeats are analyzed inside successive time windows, to derive therefrom a physiological parameter and/or a physical activity parameter of the patient with the implant, in particular as a function of a peak of amplitude of the first oscillation of the electrical signal, and of the level of this signal after the bounce phase of the signal oscillation.

12 Claims, 5 Drawing Sheets

(56) References Cited

U.S. PATENT DOCUMENTS

2010/0125309 A1 5/2010 Casset
2012/0226329 A1 9/2012 Renesto et al.
2016/0144161 A1 5/2016 Buysman et al.
2016/0151632 A1 6/2016 Makdissi

* cited by examiner

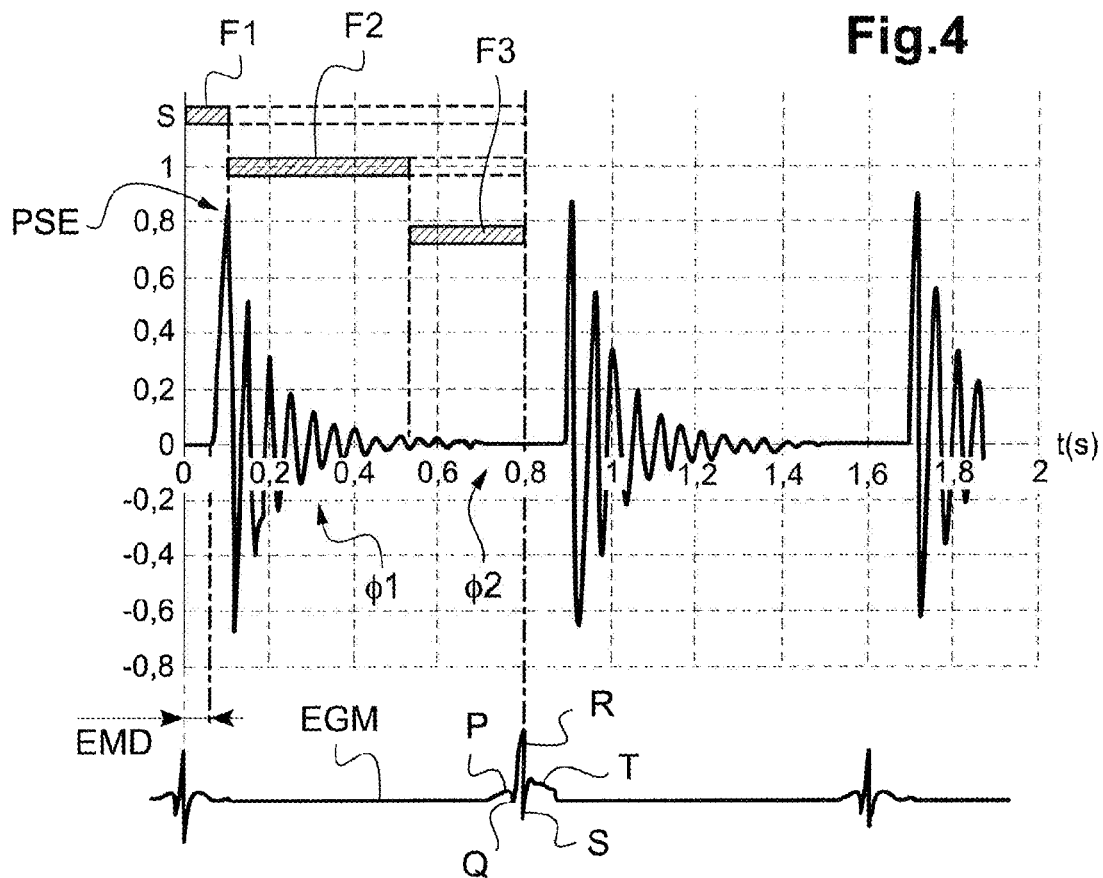
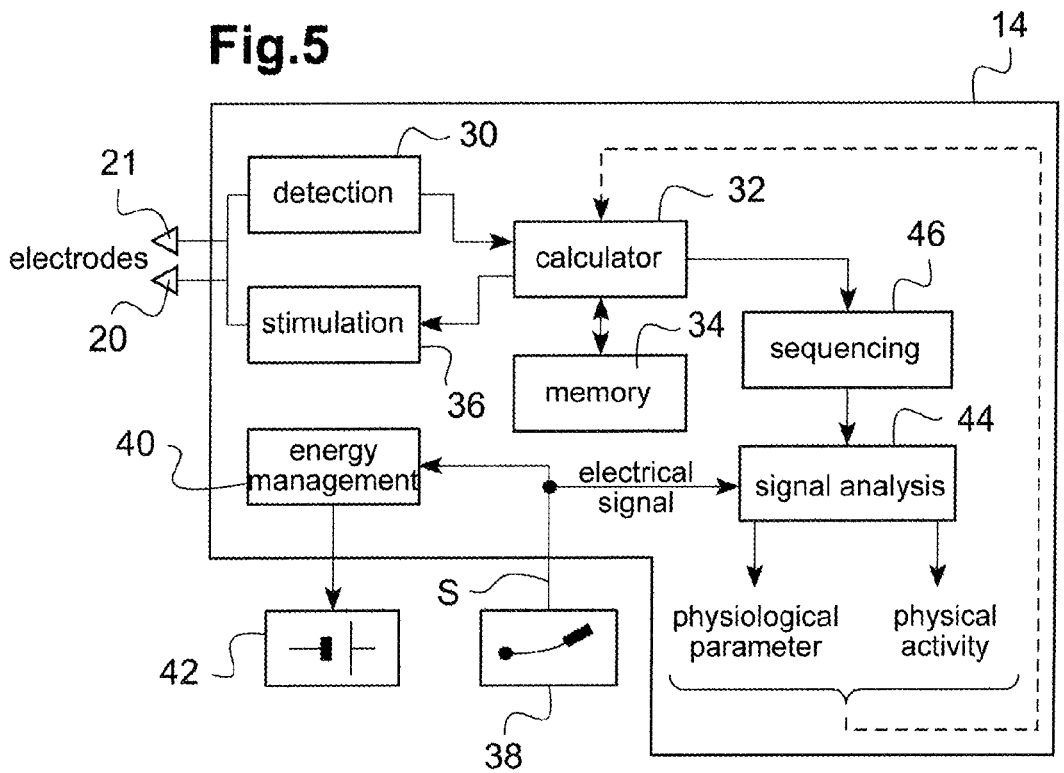

LEADLESS-CAPSULE AUTONOMOUS CARDIAC IMPLANT COMPRISING AN ENERGY HARVESTER PROVIDING PHYSIOLOGICAL OR ACTIVITY INFORMATION ABOUT THE PATIENT

CROSS-REFERENCE TO RELATED APPLICATIONS

This application is a § 371 national phase entry of International Application No. PCT/EP2018/062485, filed May 15, 2018, which claims priority to French Patent Application No. 1755938, filed Jun. 28, 2017.

BACKGROUND OF THE INVENTION

Field of the Invention

The invention relates to active implantable medical devices (AIMDs), in particular cardiac implants for monitoring the myocardium activity and issuing stimulation, resynchronization or defibrillation pulses in case of rhythm disorders detected by the device.

The invention more particularly relates to those devices which incorporate a self-powering system comprising a mechanical energy harvesting device associated with an integrated buffer battery. The harvesting device, also known as "harvester" or "scavenger", collects the mechanical energy resulting from the various movements undergone by the body of the implanted device. Those movements may have for origin a certain number of phenomena occurring at the rhythm of the heartbeats, in particular the periodic shakes of the wall on which the implant is anchored, the vibrations of the cardiac tissues linked i.a. to closings and openings of cardiac valves, or the blood flow rate variations in the surrounding environment, which stress the implant and make it oscillate at the rhythm of the flow rate variations. The mechanical energy collected by the harvester is converted into electrical energy (voltage or current), by means of a suitable mechanical-electrical transducer, for powering the various circuits and sensors of the device and for charging the buffer battery.

This energy harvesting technique is particularly well adapted for powering implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator connected to the opposite, proximal end.

In the cardiac application case, it may be epicardial leadless capsules, fixed to the outer wall of the heart, or endocavitary capsules, fixed to the inner wall of a ventricular or atrial cavity, or capsules fixed to the wall of a vessel near the myocardium. The invention is nevertheless not limited to a particular type of capsule, and is applicable as well to any other type of leadless capsule, whatever the operational purpose thereof.

The fixation of the capsule to the implantation site is made through a protruding anchoring system extending the capsule body and designed to penetrate the cardiac tissue, in particular by means of a screw. The capsule moreover comprises various electronic circuits, sensors, etc., as well as wireless communication emitter/receiver means for the remote exchange of data, the whole being integrated in a body of very small size that can be implanted at sites whose access is difficult or that leave little space available, such as the apex of the ventricle, the inner wall of the atrium, etc.

Description of the Related Art

US 2009/0171408 A1 (Solem) describes various examples of such leadless intracardial capsules.

In any case, the processing of the signals within the capsule and the remote transmission thereof require a non-negligible energy with respect to the energy resources that can be stored in the capsule in a very small available volume. Now, taking into account its autonomous character, the capsule can only use its own resources, hence the necessity for an integrated self-powering system comprising an energy harvester associated with a small integrated buffer battery.

There exist several types of energy harvesters, based on different physical principles: system of the automatic wind-up watch movement type, mobile magnet system, bellows system or similar system collecting the blood pressure variations, etc.

The invention more particularly relates to leadless capsules (or similar implantable devices) whose energy harvester uses an inertial unit subjected to the above-described external stresses, with such an inertial unit. This inertial unit may in particular implement—but non-limitatively—a transducer coupled to a pendular mechanism including in the capsule a mobile mass, called "seismic mass" or "inertial mass". This inertial mass is driven according to the movements of the capsule, which is permanently subjected to the various external stresses described hereinabove. After each of these stresses, the inertial mass, which is coupled to an elastically deformable element, oscillates at a natural frequency of free oscillation.

Other types of inertial units for energy harvester also show this phenomenon of oscillation. In any case, the invention is not limited to a particular type of inertial unit, and covers as well the units with an electromechanical transducer and those with a piezoelectric, electromagnetic, electrostatic or tribological transducer, which are all able to produce an oscillating electrical signal under the effect of an external mechanical stress and which will be denoted hereinafter by the generic word "translator".

The oscillation frequency of the inertial unit, typically of the order of a few tens of hertz, is notably higher than the frequency of the external cyclic stresses corresponding to the heartbeat frequency (at most a few hertz). Hence, at each cardiac contraction, the seismic mass (or another functionally similar mechanical element) will be stressed with a higher or lower amplitude, then the inertial system will oscillate several times with decreasing amplitudes (bounces characteristic of a damped periodic oscillation), and will finally stabilize up to the following heartbeat, where the stress/oscillations cycle will be comparably repeated.

The mechanical energy of the inertial unit oscillation is, for example, converted into electrical energy by a mechanical-electrical transducer producing an oscillating electrical signal. This signal is provided to a circuit for managing the implant power supply, which rectifies and regulates the electrical signal to output a stabilized direct voltage or current, for powering the various electronic circuits and sensors of the implant, and for charging the buffer battery.

Advantageously, but non-limitatively, the mechanical-electrical transducer may be a piezoelectric component cyclically and alternately stressed in bending so as to generate within its constituent material electrical charges that are collected at the surface of the component to be used by the self-powering system of the capsule.

The piezoelectric component may for example be a piezoelectric beam clamped at one end and coupled to the inertial mass at the other end, which is free. Reference can be made, in particular, to EP 2 857 064 A1 (Sorin CRM), which describes such an energy harvester arrangement, particularly adapted for powering a leadless capsule.

It has been proposed, besides the electrical energy harvesting, to use the electrical signal provided by the transducer to obtain information about the clinical state of the patient's heart.

Hence, above-mentioned US 2009/0171408 A1 (Solem) proposes to derive from the electrical conversion signal "energy information" making it possible to evaluate parameters such as cardiac rhythm, or amplitude or acceleration of the heartbeats. The analysis lies in the observation that the electrical energy provided by the generator, i.e. the quantity of electricity produced over a given duration, is an indicator of the kinetic energy of the heart, reflecting the acceleration and the movements of the side in which the device is implanted. In other words and in a simplified manner, the higher the electrical signal, the more it reveals a good condition of the myocardium. An evaluation of the general condition of the myocardium is hence obtained based on the mean level of energy obtained at the exit of the generator.

Comparably, US 2015/0224325 A1 (Imran) describes the possibility to also use the electrical signal of the energy harvester as a sensor signal allowing a clinical follow-up of the patient. In particular, it is possible to detect the occurrence of a fibrillation or a similar episode by a sudden drop of a mean voltage level of the electrical signal provided by the energy harvester. An alert may then be transmitted to a monitoring device, implanted or not, worn by the patient, which continuously monitors the power supply signal provided by the harvester.

The information is however, in either case, relatively brief and/or slowly evolving clinical information, derived from the mean amplitude of the electrical signal evaluated over several successive cardiac cycles.

BRIEF SUMMARY OF THE INVENTION

The object of the invention is to propose a technique for analyzing the power supply electrical signal provided by the energy harvester of an autonomous implanted device, which allows:
obtaining far more specific clinical information than the information it was possible to obtain with the known prior techniques;
in particular, obtaining such clinical information both of physiological nature (about the intrinsic behavior of the myocardium) and of physical nature (giving an indication of the patient's level of activity at a given moment); and
obtaining all this information in real time, immediately after each cardiac cycle.

It is known to obtain such information with an implanted device, in particular a device of the leadless capsule type, but it is for that purpose necessary that the capsule integrates one or several specific sensors, such as an accelerometer (G sensor) for evaluating the level of activity and/or an endocardial acceleration sensor (EA sensor) for evaluating parameters such as the contractility of the myocardium, as described, for example, in EP 3 025 758 A1 or EP 2 5 013 A1 (Sorin CRM), but in a completely different context, which is the analysis of a signal issued by an EA sensor. An EA signal has indeed nothing comparable, neither in nature nor in shape, with the damped oscillating electrical signal produced by the inertial unit of an energy harvester.

The basic idea of the invention consists in analyzing the very short term variations of the electrical signal provided by the energy harvester, between two heartbeats.

This analysis is performed in real time on the signal reflecting the oscillations of the inertial unit (typically, the oscillations of the inertial mass in the case of a pendular unit) at its oscillation frequency just after the cardiac contraction, hence corresponding to the damped oscillations or "bounces" described hereinabove, inside a same cardiac cycle.

Unlike known techniques, for example that described in above-mentioned US 2009/0171408 A1, the problem is not to analyze the evolution of the mean level of the electrical signal from one cardiac cycle to the following one, or over several successive cardiac cycles, hence to analyze far slower variations.

As will be seen, the analysis technique according to the invention allows obtaining a lot of important clinical information, both of physical and physiological nature, such as the patient's instantaneous level of activity, the degree of contractility of the myocardium, possibly by distinguishing isovolumic contraction and ventricular ejection, etc.

Advantageously, this information is obtained from the single electrical signal produced by the energy harvester, without it is required to provide the implant with one or several specific sensors, because the inertial unit (typically, the inertial mass/mechanical-electrical transducer pendular unit) plays a double role of energy harvester and physiological and/or physical activity sensor.

The invention proposes for that purpose an autonomous cardiac implant of the leadless capsule type, comprising, in a manner per se known from above-mentioned US 2009/0171408 A1: an implant body provided with means for anchoring to a cardiac wall, the implant body accommodating an electronic unit; and an energy harvesting module with an energy storage component for powering the electronic unit.

The energy harvesting module is adapted to convert into electrical energy external stresses applied to the implant body under the effect of movements of a wall to which the implant is anchored and/or of blood flow rate variations in the environment surrounding the implant at the rhythm of heartbeats and/or of cardiac tissue vibrations.

The energy harvesting module comprises: an inertial unit subjected to said external stresses; a translator adapted to convert the mechanical energy produced by the oscillations of the inertial unit into an oscillating electrical signal; and a power management circuit, adapted to rectify and regulate the oscillating electrical signal, to output a stabilized direct voltage or current for powering the electronic unit and/or for charging the energy storage component.

The device further comprises an analysis module receiving as an input the electrical signal provided by the translator and adapted to analyze variations of this oscillating electrical signal to derive therefrom a value of a physiological parameter of the patient with the implant.

Characteristically of the invention, the implant further comprises a sequencing module comprising a circuit for detecting successive ventricular or atrial cardiac events, and a windowing circuit adapted to define at least one predetermined time window between two consecutive detected cardiac events; and the analysis module is adapted to analyze the instantaneous variations of said oscillating electrical signal inside the predetermined time window(s) so defined between two consecutive detected cardiac events, and derive therefrom a current value i) of at least one physiological parameter, and/or ii) at least one physical activity parameter, of the patient with the implant.

According to various advantageous subsidiary characteristics:

- the inertial unit comprises a pendular unit with an element, elastically deformable according to at least one degree of freedom, coupled to an inertial mass. In such a case, the energy harvesting module advantageously comprises at least one piezoelectric beam coupled at one of its ends to the inertial mass, said piezoelectric beam forming both said elastically deformable element and said translator;
- the windowing circuit is adapted to define a first time window for searching for a first peak of the oscillating electrical signal;
- the windowing circuit is adapted to define a second time window corresponding to a damped free oscillation phase of the inertial unit;
- the windowing circuit is adapted to search for a peak of amplitude of the first oscillation of the electrical signal, and define the second time window as a function of the moment of said peak of amplitude;
- the analysis module is adapted to determine a quantity linked to at least a part of the duration of an alternation of the first oscillation of the electrical signal; and derive at least one physiological parameter of the patient as a function of said quantity. Said quantity is advantageously one between: the amplitude of a first signal peak of the first alternation of the oscillating electrical signal; the derivative of the amplitude of the oscillating electrical signal at the beginning of the first alternation; or the integral of the amplitude of the oscillating electrical signal over all or part of the duration of the first alternation;
- the analysis module is adapted to: discriminate a first oscillation and a second, consecutive oscillation of the electrical signal occurring in the first sub-window; determine two quantities linked to at least a part of the duration of a respective alternation of said first and second oscillations; and derive i) two distinct physiological parameters of the patient as a function of these two respective quantities or ii) a physiological parameter of the patient as a function of a combination of these two respective quantities;
- the windowing circuit is adapted to define a third time window, posterior to the second time window, corresponding to a substantially non-oscillating phase of the inertial system in damped free oscillation;
- the analysis module is adapted to: determine a quantity linked to the variations of the electrical signal during the third time window; and derive at least one physical activity parameter of the patient as a function said quantity;
- said quantity is the energy of the electrical signal, rectified and integrated, for the duration of the second sub-window.

BRIEF DESCRIPTION OF THE DRAWINGS

An exemplary embodiment of the present invention will now be described, with reference to the appended drawings, in which the same references denote identical or functionally similar elements throughout the figures.

FIG. 4 is a chronogram of the oscillations of the electrical signal provided by the energy harvesting module of the leadless capsule during successive cardiac cycles, with, opposite thereof, the corresponding electrogram curve.

FIG. 5 shows, as a block diagram, the main internal constitutive elements of the electronic unit of the leadless capsule.

DETAILED DESCRIPTION OF A PREFERRED EMBODIMENT OF THE INVENTION

An exemplary embodiment of the device of the invention will now be described.

As regards software aspects thereof, the invention may be implemented by a suitable programming of the control software of a known cardiac pacemaker device, for example a pacemaker of the endocavitary leadless capsule type.

These devices comprise a programmable microprocessor coupled to circuits for receiving, shaping and processing electrical signals collected by implanted electrodes, and providing stimulation pulses to these electrodes. The adaptation of these devices to implement the invention is within the reach of the one skilled in the art, and it won't be described in detail. In particular, it will be possible to adapt software programs that are stored in memory and executed, and to use them to implement the functions of the invention that will be described hereinafter.

The method of the invention is indeed mainly implemented by software means, with suitable algorithms executed by a microcontroller or a digital signal processor. For the sake of clarity, the various processings applied will be decomposed and schematized by a number of distinct modules or functional blocks and/or interconnected circuits, but this representation is however only illustrative, these functions or circuits having common elements and corresponding in practice to a plurality of functions generally executed by a same software program.

Figure 1:
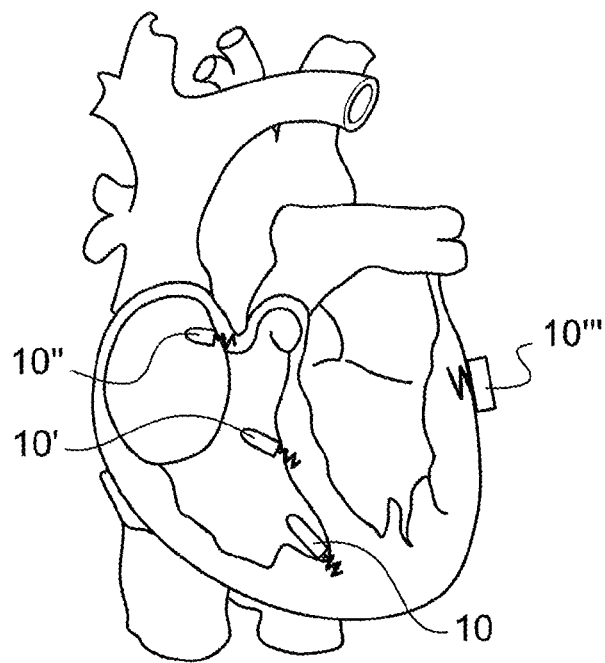
FIG. 1 illustrates a medical device of the leadless capsule type in its environment, with various examples of implantation sites in, on or near the heart of a patient.

In FIG. 1 are shown various possible sites for implanting a device of the leadless type, inside the myocardium (endocavitary implant), or on an external region of this same myocardium (epicardial implant), or also on or in a vessel close to the heart. In an advantageous preferential example, the leadless capsule 10 is implanted on the apex of the right ventricle. As a variant, the capsule may also be implanted in the right ventricle on the interventricular septum, or on a wall of the right atrial cavity, as illustrated in 10' and 10", respectively. Another configuration consists, as in 10''', in implanting the leadless capsule on an outer wall of the myocardium.

In any case, the leadless capsule is fixed to the cardiac wall by means of a protruding anchoring screw intended to penetrate the cardiac tissue by being screwed to the implantation site. Other anchoring systems can be used, and modify in no way the implementation of the present invention.

Figure 2:
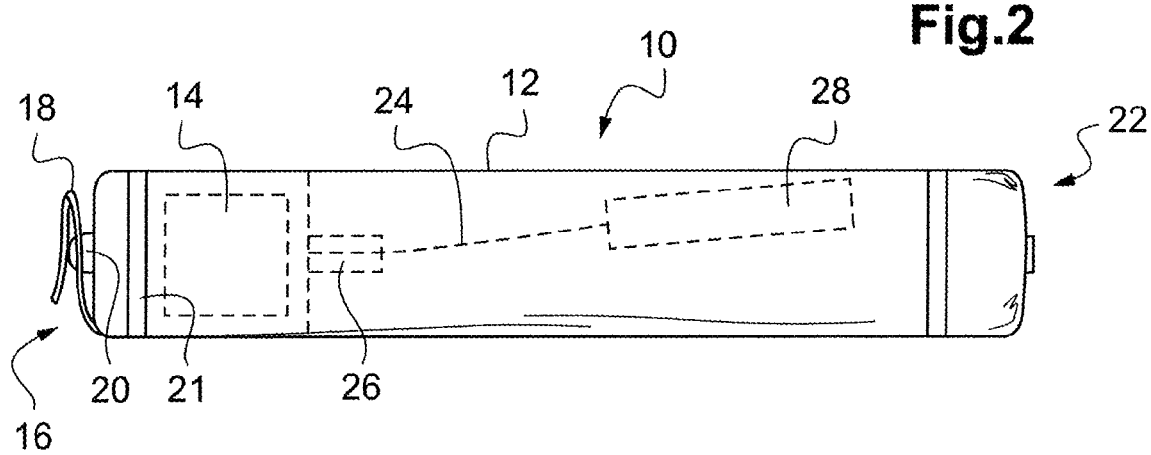
FIG. 2 is a generally side view of a leadless capsule comprising an energy harvester with a pendular unit.

FIG. 2 is a general side view of such a leadless capsule, comprising an energy harvester with a pendular unit.

In this example, the leadless capsule 10 is made in the external form of a cylindrical tubular implant body 12 enclosing a unit 14 including the various electronic and power supply circuits of the capsule. The typical dimensions of such a capsule are a diameter of the order of about 6 mm for a length of about 25 mm.

At the distal end 16 thereof, the capsule carries an helical screw 18 for anchoring the capsule against a wall of a cardiac cavity, as illustrated hereinabove in relation to FIG. 1. A detection/stimulation electrode 20, in contact with the cardiac tissue at the implantation site, collects cardiac depolarization potentials and/or applies stimulation pulses. In certain embodiments, the function of the electrode 20 is provided by the anchoring screw 18, which is then an active screw, electrically conductive and connected to the detection/stimulation circuits of the capsule. The electrode 20 in contact with the tissues is generally a cathode, and it is associated with an anode whose function is provided by a second, remote electrode, most often an annular electrode, as in 21.

The opposite proximal end 22 of the leadless capsule 10 has an atraumatic rounded shape and is provided with suitable gripping means for the link to a guide-catheter or another implantation accessory usable at the moment of implantation or explantation of the capsule.

The leadless capsule 10 is provided with an energy harvesting module for powering the electronic unit 14 and/or for charging an integrated battery or an energy storage capacitor.

Such an energy harvesting module comprises an inertial unit that, inside the capsule, oscillates following the various external stresses to which the leadless capsule is subjected. These stresses may in particular result from: the movements of the wall to which the capsule is anchored, which are transmitted to the implant body 12 by the anchoring screw 18; and/or the blood flow rate variations in the environment surrounding the implant, which produce oscillations of the implant body at the rhythm of the heartbeats; and/or the various vibrations transmitted by the cardiac tissues.

Figure 3:
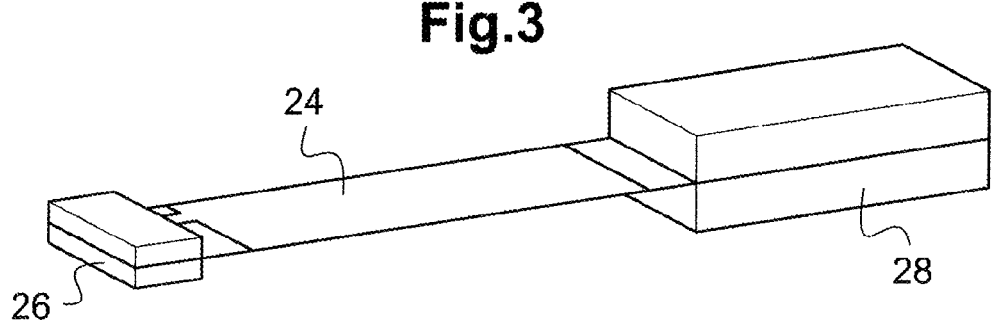
FIG. 3 shows separately the pendular unit of the leadless capsule of FIG. 2, with a piezoelectric beam coupled to an inertial mass.

FIG. 3 illustrates an example of inertial unit for an energy harvesting module, a unit that is herein made up by a piezoelectric beam 24 clamped at one of its ends 26 and whose opposite, free end is coupled to an inertial mass 28. The piezoelectric beam 24 is a flexible beam that, in the illustrated example, is elastically deformable according to at least one degree of freedom in longitudinal bending.

From a mechanical point of view, this unit constitutes a pendular unit of the mass-spring type (the spring being formed by the flexible piezoelectric beam) that, due to the inertia of the mass 28, oscillates as soon as the piezoelectric beam 24 is spaced apart from its stable rest position. Actually, this unit may be equated, as for its mechanical behavior, to a structure of the "clamped/free beam" type, having a natural frequency of free oscillation, which is herein the frequency at which the mass-spring system oscillates.

The piezoelectric beam 24 further performs a function of mechanical-electrical transducer making it possible to convert into electrical charges the mechanical stress that is applied to it when it is bent, these charges being collected by electrodes formed at the surface of the beam. The beam is preferably a beam of the bimorphous type, i.e. capable of generating energy on its two faces when subjected to a deformation. Theses transduction properties are typical of a piezoelectric material, such as PZT ceramics or monocrystals of the PMN-PT, barium titanate or lithium niobate type.

Of course, the invention is not limited to this particular configuration of pendular unit given as an example, and other types of inertial units may be used for the energy harvesting, such as those mentioned in introduction, from the moment that they have at least one natural frequency of free oscillation.

Likewise, the inertial unit may be a unit deformable according to several degrees of freedom, with then as many corresponding vibration modes and natural frequencies of oscillation, and electrical signals respectively output.

FIG. 4 is a chronogram of the oscillations of the electrical signal S provided by the energy harvesting module of the leadless capsule during successive cardiac cycles, with, opposite thereof, the corresponding electrogram curve.

The electrogram signal, EGM, which is the electrical signal of the cardiac depolarization wave, is for example detected by the electrode 20 in contact with the myocardium. In the example illustrated in FIG. 4, the electrogram is that of a sinus rhythm, with a wave P corresponding to the atrial electrical activity, a QRS complex corresponding to the ventricular electrical activity and a wave T corresponding to the ventricular repolarization. Signal filtering and processing means, included in the circuits of the unit 14, make it possible to easily derive from the EGM a time marker R indicating the moment of the ventricular depolarization. If the depolarization results from an electrical stimulation issued by the leadless capsule, the corresponding marker V corresponds to the moment when the pulse is issued. It is also possible to obtain in the same way markers of the atrial electrical activity, P (spontaneous) or A (stimulated).

Hereinafter, reference will mainly be made to a R marker (spontaneous ventricular depolarization), but it is advisable to equate this case to that of a V marker (stimulated ventricular depolarization) or a P/A marker (spontaneous or stimulated atrial depolarization).

This mode of detection of the cardiac events (ventricular events or atrial events) based on an EGM signal collected by a system of electrodes is however not limitative, and there exist other techniques of detection, in particular techniques of detection of mechanical nature (non-electrical), such as those obtained by analysis of the signal provided by an accelerometer integrated to the implant, this accelerometer providing a signal representative of the endocardial acceleration (EA).

EP 3 025 758 A1 describes such a technique, in which the leadless capsule comprises an EA sensor whose signal is analyzed to detect the capture or the absence of capture (presence or not of a contraction of the ventricle) following the application of a stimulation pulse. However, in such a known technique, these signals are no longer connected to the electrical activity of the myocardium, but to its mechanical activity.

FIG. 4 also illustrates, opposite the electrogram EGM, the variations of the electrical signal S provided by the energy harvester, i.e. the variable signal produced by the mechanical-electrical transducer made up by the piezoelectric beam 24, in the illustrated example. This signal is a recurrent signal, repeated at the rhythm of the successive heartbeats, and it has, at each occurrence, two characteristic phases that follow each other, Ø1 and Ø2.

The first phase Ø1 is made up of a succession of damped sinusoidal oscillations, with a first peak of amplitude followed by a series of "bounces" of decreasing amplitudes. The first oscillation of this phase Ø1 occurs after a delay EMD, called "electromagnetic delay", corresponding to the physiological delay between i) the occurrence of the depolarization wave (spontaneous or stimulated) at the ventricular tissues, and ii) the mechanical contraction of the myocardium produced by this depolarization wave.

The first phase Ø1 of damped oscillations is followed by a second, consecutive phase Ø2, substantially without bounces, that continues up to a new contraction of the myocardium producing similar variations of the signal S.

The order of magnitude of the repetition frequency of the cardiac cycles is typically of 1 to 2 Hz (60 to 120 bpm (beats per minute)). The natural frequency of the pendular unit is determined by the geometry of the piezoelectric beam 24 (mainly its length and thickness), by the elasticity of the material from which it is composed, and by the mass of the inertial mass 28. These different parameters are chosen so as to give to the natural frequency of free oscillation a far higher value than the frequency of the cardiac rhythm, for example a frequency of the order of 20 Hz, this value being of course not limitative in any way. What is important is that, in almost any circumstances, between two heartbeats the pendular unit should produce a plurality of bounces followed by a phase without bounces before the following heartbeat.

FIG. 5 is a synoptic representation of the electronic unit 14 integrated into the leadless capsule 10, shown as functional blocks. This circuit 14 is advantageously implemented as an ASIC or a combination of ASICs.

Block 30 denotes a circuit for detecting the cardiac depolarization wave, connected to the electrode 20 in contact with the cardiac tissue and to the opposite electrode 21. Block 30 comprises filters and means for analog and/or digital processing of the signal collected. The so-processed signal is applied to the input of a calculator 32 associated with a memory 34. The calculator 32 operates based on the signals collected from a detection of the successive ventricular or atrial cardiac events, so as to generate (inter alia) a series of successive markers R/V (and/or P/A) at the rhythm of the heartbeats.

The electronic unit 14 also includes a stimulation circuit 36 operating under the control of the calculator 32 for, as and whenever necessary, providing myocardium stimulation pulses to the system of electrodes 20 and 21 and generating corresponding markers V or A.

An energy harvesting circuit 38 is moreover provided, made up by the pendular unit formed by the piezoelectric beam 24 and the inertial mass 28 described hereinabove with reference to FIGS. 2 and 3.

This energy harvesting circuit 38 outputs a variable electrical signal S, whose variations are illustrated in various situations, in particular in FIG. 4 and FIGS. 6 to 8.

First, the signal S is provided to a power management circuit 40, which rectifies and regulates the signal S so as to output a stabilized direct voltage or current for powering the electronic unit 14 and charging a buffer battery 42 or a similar device such as an energy storage capacitor.

Secondly, this same signal S is applied to a circuit 44 for analyzing the instantaneous variations of the signal in order to output, characteristically and as described hereinafter, at least one physiological parameter of the patient with the implant and/or at least one physical activity parameter of this same patient (or, at the very least, state data making it possible to derive these parameters). These parameters will in particular be usable by the calculator 32 to provide a short-term, mean-term or long-term follow-up of the patient's state, and to modulate, as and whenever necessary, the application of the stimulation pulses by the circuit 36.

The analysis circuit 44 operates under the control of a sequencing circuit 46 that defines the time position of one or several analysis windows on the basis of determined electrical cardiac events (R/V and/or P/A) by the calculator 32, these windows delimiting the various processings performed by the circuit 44 in order to extract from the raw signal S the desired significant information.

Advantageously, as illustrated in FIG. 4, three windows F1, F2 and F3 are provided, successively triggered by the sequencing circuit 46.

The first window F1 is for polling the signal S, triggered upon detection of a spontaneous or stimulated cardiac event (ventricular event in the example illustrated).

The function of window F1 is to begin following up and analyzing the variations of the electrical signal S, so as to detect therein the occurrence of the first maximum of the free oscillation of the pendular unit (piezoelectric beam 24 and inertial mass 28). This first maximum is the electrical signal peak PSE in FIG. 4.

The search for the peak PSE, as well as the following steps, will be detailed hereinafter with reference to FIG. 9.

Other criteria can be contemplated for triggering the signal polling window F1, as a variant or as a complement to a simple detection of the electrical signal peak PSE, in particular:

upon detection of the cardiac event, applying a fixed or parameterizable delay before triggering window F1, in particular to take into account the elapse of an electromechanical delay EMD: a variation of the signal that would be detected in this interval would indeed correspond to an artefact, to be ignored in the search for the oscillation peak; or applying a similar delay, but variable cycle-by-cycle as a function of the cardiac rhythm, for example a delay calculated as a percentage of the preceding interval RR (or VV, RV or VR).

Obtaining a Physiological Parameter of the Patient

Figure 6:
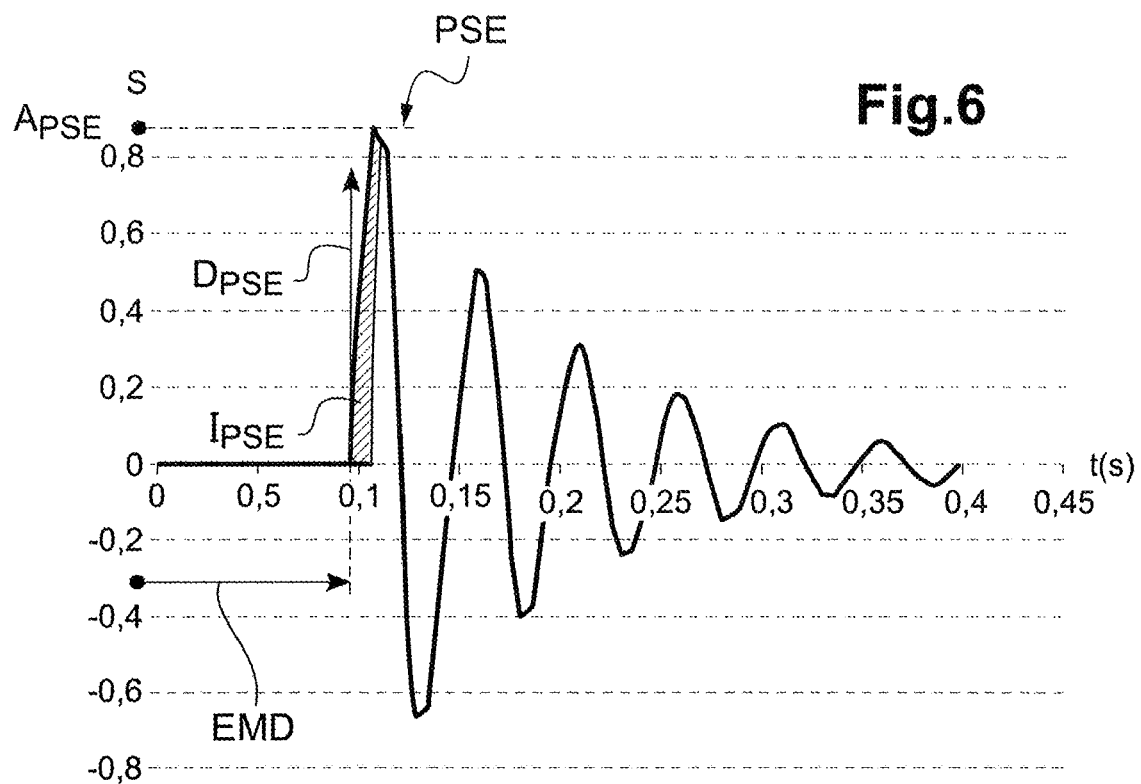
FIG. 6 is a chronogram of the electrical signal oscillations, illustrating in particular the features of the first oscillation to be analyzed, in order to derive therefrom one or several physiological parameters specific of the patient with the leadless capsule.

FIG. 6 more particularly illustrates various possible manners to derive information representative of a physiological parameter of the patient once the electrical signal peak PSE detected, in particular based on:

the maximum amplitude $A_{PSE}$ of the electrical signal S (i.e. the level of amplitude of the peak PSE);

a derivative of the amplitude of the electrical signal S at the beginning of the first alternation (of the PSE), as illustrated in FIG. 4 by the slope $D_{PSE}$ of the signal S;

an integration of the amplitude of the electrical signal S over all or part of the duration of the first alternation, for example, as illustrated in FIG. 4, over the portion $I_{PSE}$ of the first half-alternation that is comprised between the moment of the alternation beginning and the moment of the peak PSE.

Each of these data, or a combination of these data, allows deriving a physiological parameter of the patient, representative in particular of the myocardium contractility.

As a complement, the duration elapsed between the moment of detection of the cardiac event and the moment of beginning of the first oscillation of the signal, which is a duration corresponding to the electromagnetic delay EMD, may also provide relevant information about the myocardium contractility.

The so-determined physiological parameter(s) may be memorized in a memory of the device for diagnosis purpose, according to techniques of analysis per se known and that do not belong to the invention, in particular techniques of:
analyzing the short-term variations, cycle-by-cycle, of the parameter(s), in particular for detecting a situation of beginning of infarction;
analyzing the variations over the mean term, of the order of a few days, of the parameter(s), in particular for diagnosing slowly evolving pathologies such as ischemia or cardiac decompensation;
analyzing the variations over the long term, of the order of a few weeks or a few months, of the parameter(s), for evaluating very slowly evolving pathologies, in particular within the framework of prevention or follow-up of cardiac failure.

Figure 7:
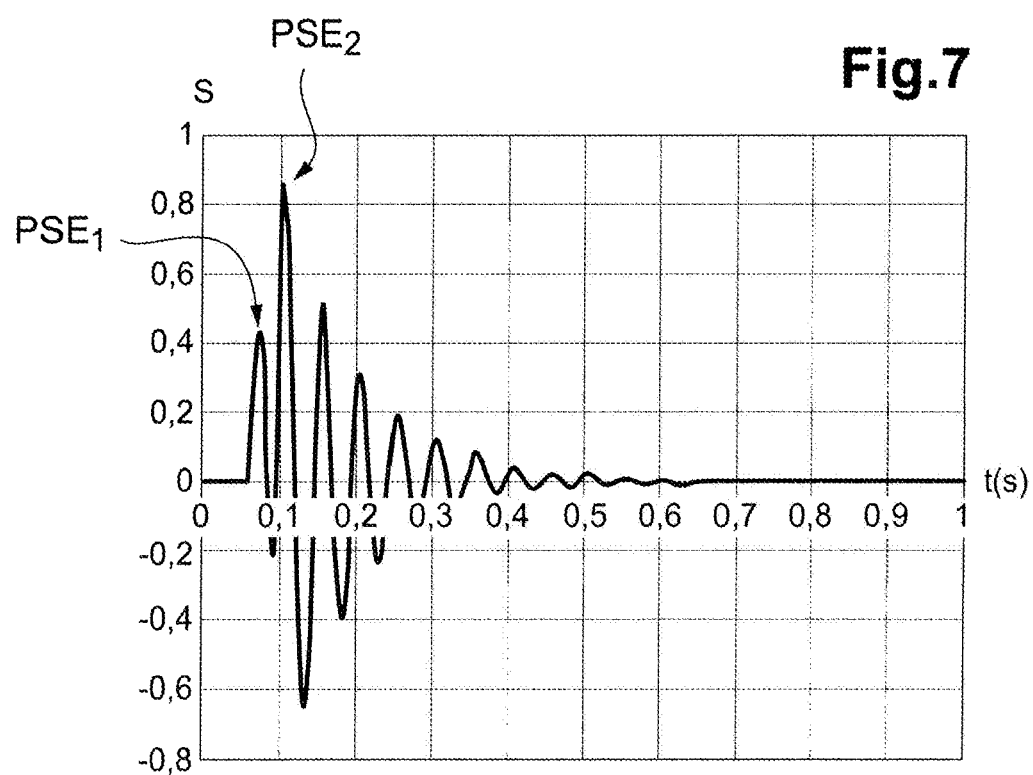
FIG. 7 is a chronogram of the electrical signal oscillations, illustrating the possibility to discriminate the two isovolumic contraction and ventricular ejection phases of a same cardiac cycle, to allow a specific analysis of the cardiac contractility over these two phases.

FIG. 7 illustrates another possibility offered by the technique of the invention, which allows discriminating in certain configurations the main successive components of the myocardium contraction, i.e. the isovolumic contraction and ii) the immediately consecutive ventricular ejection.

This discrimination is performed by analyzing the two first peaks of the electrical signal S: if a first minor peak PSE1 immediately followed by a second major peak PSE2, of higher amplitude, are detected on this signal, as illustrated in FIG. 7, this means that the first peak PSE1 is that produced by the isovolumic contraction and the second peak PSE2 is that produced by the ventricular ejection (it will be noted that these two peaks, which are distinguishable in the example of FIG. 7, are on the other hand merged with each other into a same peak PSE in the chronogram examples of FIGS. 4 and 6).

Once determined the moments of occurrence and the amplitudes of each of the peaks PSE1 and PSE2, the device may derive from this information one or several physiological and/or physical activity parameters of the patient, based in particular on:
the peak amplitude of the first peak PSE1 (value linked in particular to the patient's level of activity);
the moment of occurrence of the first peak PSE1;
the time interval separating the two peaks PSE1 and PSE2.

The combined analysis of information about the isovolumic contraction and about the ventricular ejection, respectively, is a technique per se known, for example from EP 2 495 013 A1 and EP 2 684 515 A1, in which this information is obtained from an endocardial acceleration (EA) signal, which is a signal of mechanical origin issued by an accelerometer sensor arranged, for example, at the end of an endocavitary lead implanted in the bottom of the ventricle.

In any case and generally, as a variant or as a complement to the use for diagnosis purposes of the physiological parameter(s) obtained by the technique of the invention, such parameter(s) may be used for controlling the cardiac stimulation frequency.

Indeed, as the cardiac contractility increases with the effort, this physiological parameter may be used to control the rhythm of delivery of the stimulation pulses, in the case where the patient is not in sinus rhythm, but is stimulated by the implanted device.

Obtaining a Physical Activity Parameter of the Patient

The function of the two following windows F2 and F3 will now be described.

The detection of the peak PSE triggers a second window F2 (FIG. 4), which is a bounce phase cancelling window.

The function of window F2 is to analyze the variations of the signal S so as to delimit the phase Ø1 of the successive bounces (damped oscillations) of the pendular unit, to determine a moment when this bounce phase Ø1 will be considered as ended.

The end of the bounce phase may be defined according to several possible criterial, possibly combinable with each other, such as:
duration, fixed or parameterizable, counted from the moment of detection of the first peak PSE of the signal S;
variable duration as a function of the cardiac rhythm, for example a duration of 50% of the preceding interval RR, or an average of the preceding intervals RR;
amplitude of the signal S becoming, over at least one complete oscillation, lower than a given threshold, which may be a fixed or parameterizable threshold or a variable threshold corresponding to a given percentage (for example 5%) of the amplitude of the peak PSE;
variability of the signal S becoming lower than a given threshold: indeed, due to the dampening of the sinusoid, this variability decreases with the successive oscillations.

The determination of the end of the bounce phase (end of phase Ø1) has for effect to trigger a third window F3, which is a patient's activity detection window.

Window F3 extends over a duration (phase Ø2) comprised between the end of the damped sinusoid and the beginning of the following cardiac contraction. Insofar as the pendular unit has finished its phase of free oscillation consecutive to the cardiac contraction (phase Ø1), the variations of the signal that may be detected in all or part of window F3 do not come from the cardiac contraction, but from stresses external to the myocardium. Concretely, the stresses essentially result from movements of the patient, i.e. his/her own physical activity level: walking, mounting stairs, doing exercise, various movements of the chest, etc., which induce irregular movements of the inertial mass, hence deformations of the piezoelectric beam and consequently production of electrical charges and of a corresponding voltage or current at the output of the energy harvester.

The evaluation of this level of activity may in particular be obtained by rectification and integration of the signal S over all or part of the duration of window F3.

Figure 8A:
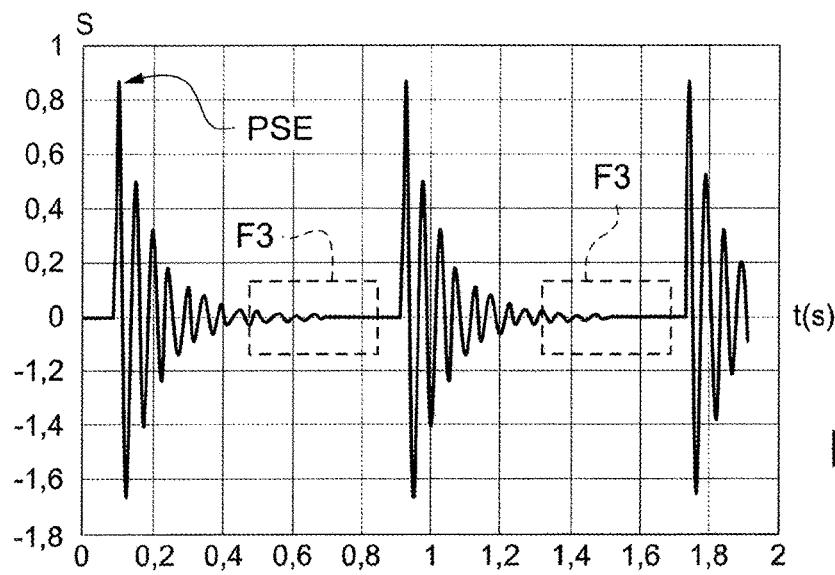
FIGS. 8a to 8c are chronograms of the electrical signal oscillations, illustrating the way to analyze this signal after the bounce phase, so as to derive therefrom a instantaneous physical activity parameter of the patient with the leadless capsule.
Figure 8B:
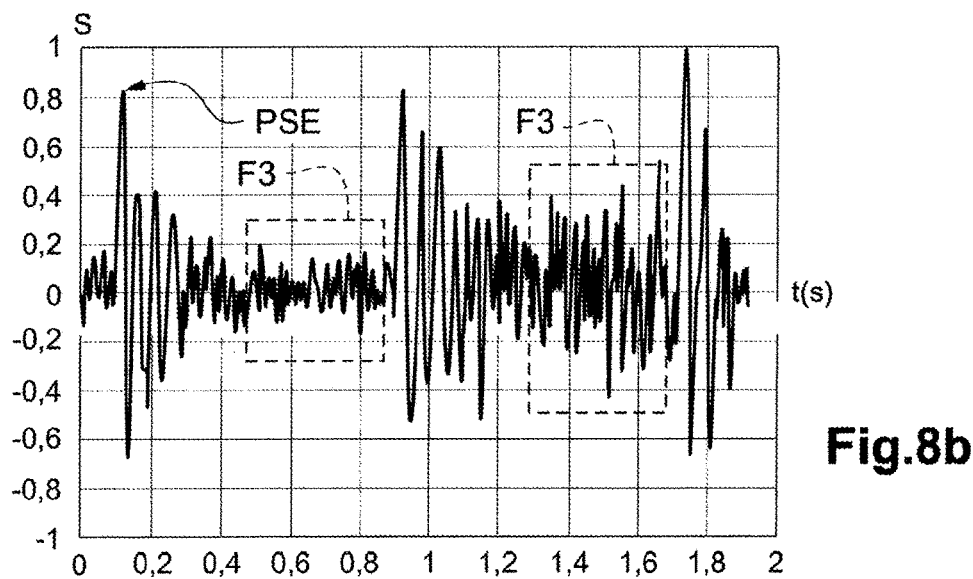
Figure 8C:
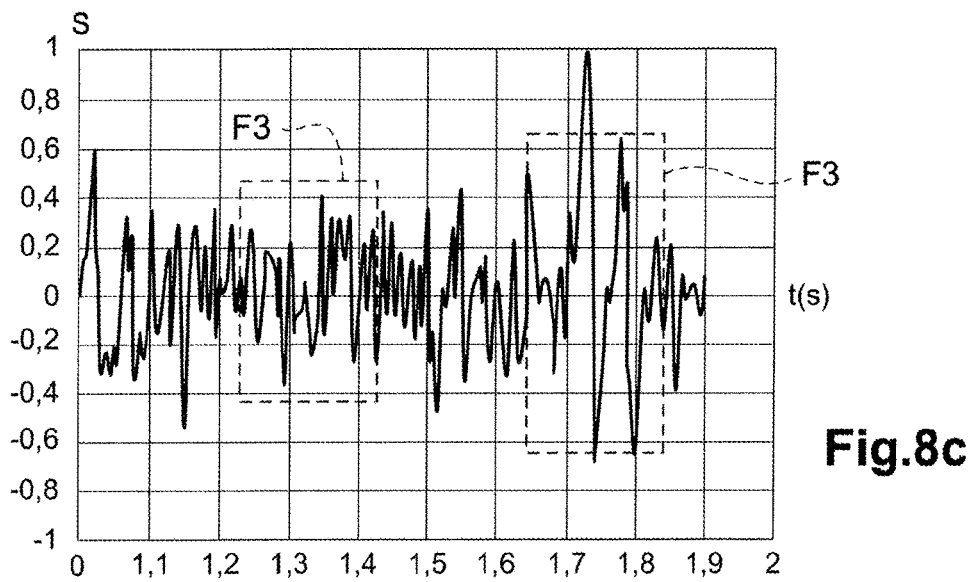

FIGS. 8a to 8c illustrate examples of variation of the electrical signal S in various situations of patient's activity.

FIG. 8a is an example of signal collected when the patient is at rest. The bounce phase is followed with a phase, indicated in dotted line and corresponding to window F3, during which the variations of the signal S are very low, or even imperceptible, up to the occurrence of the following cardiac cycle.

On the other hand, in the case of FIG. 8b, the patient's activity increases, with a far higher signal variation level over the duration of window F3.

The patient's activity parameter is advantageously evaluated by rectifying and integrating the signal S over the duration of window F3, i.e. by summing the absolute values of the signal samples successively collected during this period.

FIG. 8c illustrates an example in which the level of activity is even higher, typically corresponding to a situation of intense exercise such as running, mounting stairs, etc. It may even happen that, in this case, the mean level of the signal S in the patient's activity detection window F3 is higher than the mean level of the signal out of this window, in particular in periods corresponding to the signal polling window F1 for searching for the first peak of free oscillation of the pendular unit and to the bounce phase cancelling window F2 described with reference to FIG. 4.

In such a case, window F3 can no longer be defined by the above-mentioned techniques (detection of the first peak PSE, then application of a bounce phase cancelling window F2), because the electrical signal variations have longer the behavior they previously had, as in the case of FIGS. 8a and 8b where it is possible to easily discriminate the peak PSE characterizing the beginning of the free oscillation of the pendular unit. As window F3 can no longer be determined by analysis of the signal during the current cycle, it can be determined, for example, based on the value this window had at the preceding cycles, by keeping the same time position with respect to the cardiac event, and by keeping the same window duration or by adjusting this duration by a predetermined factor (for example of 10 ms or 10%) to take into account the fact that an increase of the activity is very probably accompanied with an acceleration of the cardiac rhythm, which will have to be taken into account for defining the window.

As a variant, the duration of window F3 may be determined based on the current cardiac rhythm, for example as a percentage of the current interval RR, possibly averaged over the few preceding cycles, this window being offset by a predetermined duration with respect to the ventricular contraction detection marker (marker that is given by the analysis of the signal EGM, independent from the mechanical disturbances produced by the intense activity of the patient).

Figure 9:
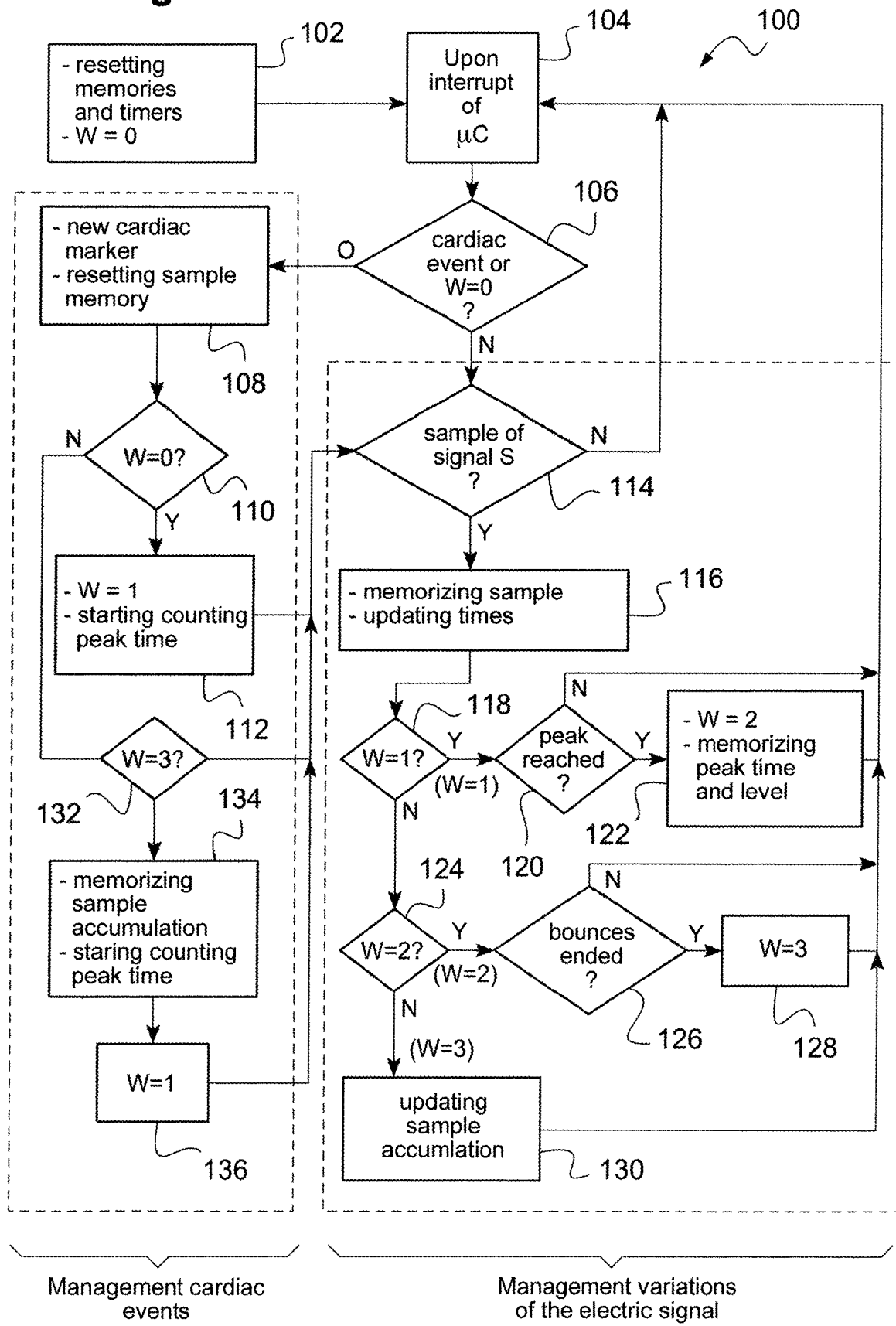
FIG. 9 is a flow diagram showing in detail, according to an illustrative example of implementation of the invention, the sequence of operations and tests performed on the electrical signal provided by the energy harvesting module, as a function of the detected cardiac events, for obtaining data making it possible to determine physiological and physical activity parameters.

FIG. 9 is a flow diagram 100 describing in detail, according to an illustrative example of implementation of the invention, the sequence of operations and tests performed on the electrical signal S provided by the energy harvesting module as a function the cardiac events detected, in order to obtain data that will make it possible to determine one or several physiological and/or physical activity parameters.

Block 102 corresponds to a previous step of resetting the various memories and timers that will be used afterwards. A parameter W is also reset, this parameter indicating the phase of analysis in which the algorithm is during its various successive iterations, and can take the following values:

W=0: initial value, undetermined phase,
W=1: electrical signal polling phase for searching for the first peak (peak PSE in FIG. 4), corresponding to window F1 in FIG. 4 and during which the signal S produces significant information for obtaining a physiological parameter,
W=2: bounce phase cancelling phase, corresponding to window F2 of FIG. 4, during which the signal does not produce significant information for obtaining a physical or physiological parameter,
W=3: phase posterior to the bounce phase, corresponding to window F3 of FIG. 4 and during which the signal S produces significant information for obtaining a physical activity parameter.

The algorithm is regularly iterated at each receipt of a sequencing pulse corresponding to an interruption provided by the microprocessor (block 104).

If a cardiac event (typically a marker R or V) is detected, or if the nature of the window is not yet determined (W=0), the test 106 directs the algorithm towards a set of steps 108 and following, for cardiac event management.

At block 108, a new cardiac marker is established, and the memory of the samples of the signal S is reset.

If this is the first iteration (i.e. if W=0, test 110), then the window indication W is set at 1 and a timer is started (block 112) so as to trigger the polling of the electrical signal for searching for the signal peak (peak PSE).

At each received sample of the signal S (test 114), the sample is memorized and the times measured are updated (block 116). If the process is still in phase of searching for the signal peak (W=1, test 118), as long as the peak is not reached, i.e. as long as the level of the signal S increases, then the algorithm is iterated (test 120, return to step 104). In the opposite case, the moment of occurrence and the level of the peak PSE are memorized (block 122), and, the peak searching phase being ended, the indicator W is set at W=2. This iteration of the flow diagram is terminated with a return to step 104.

During the bounce phase (W=2, test 124), the successive signal samples are analyzed to determine if this bounce phase is ended, according to the various criteria that are explained hereinabove (signal level above a given threshold, elapse of a maximum time, etc.). If the process is still in bounce phase (test 126), the algorithm is iterated (return to block 104). In the contrary case, the indicator W is set at W=3 (block 128).

At each iteration, the algorithm will collect a new sample and cumulate it with the previous ones (block 130) for, as explained hereinabove, rectifying and integrating the signal over the whole duration of the activity detection window (W=3).

These iterations will continue up to the detection of a new cardiac event (test 106).

This new cardiac event, detected by test 132, will trigger (block 134) various operations of cycle analysis ending, with, in particular, memorizing the accumulation of the samples previously obtained at block 130, and will trigger the counting of the time for determining the moment of occurrence of the next peak of the electrical signal (this operation of block 134 being the same as that which was performed at the resetting in block 112). The window indicator is then set at W=1 (block 136) to indicate that the process is again in a signal polling window.

The algorithm then returns to step 114 for waiting for a new sample of the signal S, which will be processed in the same way as described hereinabove.

The invention claimed is:

1. An autonomous cardiac implant of a leadless capsule type, having an implant body provided with means for anchoring to a cardiac wall, the implant body accommodating an electronic unit and an energy harvesting module with an energy storage component for powering the electronic unit, the energy harvesting module being adapted to convert into electrical energy external stresses applied to the implant body under an effect of movements of a wall to which the implant is anchored and/or of blood flow rate variations in an environment surrounding the implant at a rhythm of heartbeats and/or of cardiac tissue vibrations, wherein the energy harvesting module comprises:
- an inertial unit subjected to said external stresses;
- a translator adapted to convert the mechanical energy produced by oscillations of the inertial unit into an oscillating electrical signal; and
- a power management circuit, adapted to rectify and regulate said oscillating electrical signal, to output a stabilized direct voltage or current for powering said electronic unit and/or for charging said energy storage component, the implant further comprising an analysis module receiving as an input the oscillating electrical signal provided by the translator, and a sequencing module, comprising:
- a circuit for detecting successive ventricular or atrial cardiac events; and
- a windowing circuit, adapted to define at least one predetermined time window between two consecutive detected cardiac events;

wherein the analysis module is adapted to:
- analyze instantaneous variations of said oscillating electrical signal inside said at least one predetermined time window so defined between two consecutive detected cardiac events, and
- derive therefrom a current value i) of at least one physiological parameter, and/or ii) at least one physical activity parameter, of the patient with the implant.

2. The implant of claim 1, wherein the inertial unit comprises a pendular unit with an element, elastically deformable according to at least one degree of freedom, coupled to an inertial mass.

3. The implant of claim 2, wherein the energy harvesting module comprises at least one piezoelectric beam coupled at one of its ends to the inertial mass, said piezoelectric beam forming both said elastically deformable element and said translator.

4. The implant of claim 1, wherein the windowing circuit is adapted to define a first time window for searching for a first peak of the oscillating electrical signal.

5. The implant of claim 4, wherein the analysis module is further adapted to
- determine a quantity linked to at least a part of a duration of an alternation of the first oscillation of the electrical signal; and
- derive the at least one physiological parameter of the patient as a function of said quantity.

6. The implant of claim 5, wherein said quantity is one between:
- an amplitude of a first alternation of the oscillating electrical signal;
- a derivative of an amplitude of the oscillating electrical signal at the beginning of the first alternation; or
- an integral of the amplitude of the oscillating electrical signal over all or part of the duration of the first alternation.

7. The implant of claim 4, wherein the analysis module is further adapted to:
- discriminate a first oscillation and a second, consecutive oscillation of the electrical signal occurring in a first sub-window;
- determine two quantities linked to at least a part of a duration of a respective alternation of said first and second oscillations; and
- derive i) two distinct physiological parameters of the patient as a function of these two respective quantities or ii) a physiological parameter of the patient as a function of a combination of these two respective quantities.

8. The implant of claim 1, wherein the windowing circuit which is further adapted to additionally define a second time window corresponding to a damped free oscillation phase of the inertial unit.

9. The implant of claim 8, wherein the windowing circuit is further adapted to search for a peak of amplitude of the first oscillation of the electrical signal, and define the second time window as a function of the moment of said peak of amplitude.

10. The implant of claim 8, wherein the windowing circuit is adapted to define a third time window, posterior to the second time window, corresponding to a substantially non-oscillating phase of the inertial system in damped free oscillation.

11. The implant of claim 10, wherein the analysis module is further adapted to:
- determine a quantity linked to the variations of the electrical signal during the third time window; and
- derive at least one physical activity parameter of the patient as a function of said quantity.

12. The implant of claim 11, wherein said quantity is the energy of the electrical signal, rectified and integrated, for a duration of the second sub-window.

* * * * *